United States Patent [19]

Login et al.

[11] Patent Number: 4,830,850
[45] Date of Patent: May 16, 1989

[54] QUATERNIZED NITROGEN CONTAINING COMPOUNDS

[75] Inventors: Robert B. Login, Oakland; Ratan K. Chaudhuri, Butler; David J. Tracy, Lincoln Park; Michael W. Helioff, Westfield, all of N.J.

[73] Assignee: GAF Corporation, Wayne, N.J.

[21] Appl. No.: 91,008

[22] Filed: Aug. 28, 1987

Related U.S. Application Data

[63] Continuation-in-part of Ser. No. 922,923, Oct. 24, 1986, Pat. No. 4,732,990.

[51] Int. Cl.$^4$ ................................. A61K 7/09
[52] U.S. Cl. ........................... 424/70; 424/45; 424/54; 424/59; 424/71; 424/73; 424/78; 424/DIG. 4; 514/847; 514/881; 514/183; 514/212; 514/327; 514/315; 514/424; 252/8.8; 252/8.9; 540/451; 540/531; 546/221; 546/216; 546/243; 548/550
[58] Field of Search ................. 540/451, 531; 546/243, 546/221, 243; 548/550; 514/183, 212, 351, 424, 881, 847; 424/70, 71, 72, DIG. 3, DIG. 4, 62, 63, 64, 69; 252/8.8

[56] References Cited

U.S. PATENT DOCUMENTS

| | | | |
|---|---|---|---|
| 3,145,147 | 8/1964 | Glickman | 132/7 UX |
| 4,540,507 | 9/1985 | Grollier | 252/542 X |
| 4,612,188 | 9/1986 | Zorayan et al. | 424/71 X |
| 4,732,990 | 3/1988 | Login et al. | 540/451 |
| 4,760,152 | 7/1988 | Tracy et al. | 546/243 X |

FOREIGN PATENT DOCUMENTS 1326561  4/1963  France ................................. 424/71

OTHER PUBLICATIONS

Noller, "Chemistry of Organic Compounds", 1965, 3rd Ed., p. 253.

*Primary Examiner*—Joseph Paul Brust
*Attorney, Agent, or Firm*—Marilyn J. Maue; Joshua J. Ward

[57] ABSTRACT

The invention relates primarily to quaternized compounds having the formula

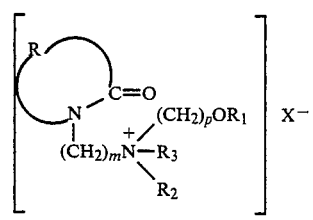

wherein m and p are each integers having a value of from 1 to 4; R is alkylene having from 3 to 8 carbon atoms and is optionally substituted with $C_1$ to $C_4$ alkyl; $R_1$ is alkyl or alkenyl having from 1 to 30 carbon atoms; $R_2$ and $R_3$ are each independently selected from the group of —$(CH_2)_pOR_1$, alkyl, alkylhydroxy, aryl, aralkyl, aralkenyl, alkaryl, and alkylene amidoalkyl radicals, said $R_2$ and $R_3$ groups having from 1 to 30 carbon atoms and at least one of $R_1$, $R_2$ and $R_3$ is a radical having from 8 to 30 carbon atoms; and $X^-$ is a chloride, bromide or iodide anion. The invention also relates to the preparation and use of said quaternized compounds.

19 Claims, No Drawings

QUATERNIZED NITROGEN CONTAINING COMPOUNDS

This application is a continuation-in-part of co-pending U.S. patent application Ser. No. 922,923, filed Oct. 24, 1986 entitled QUATERNIZED NITROGEN CONTAINING COMPOUNDS now U.S. Pat. No. 4,732,990 issued Mar. 23, 1988.

In one aspect the invention relates to novel quaternized compounds which possess viscosity enhancing and hair conditioning properties, particularly in the presence of anionic surfactants. In another aspect the invention relates to novel quaternized compounds having bactericidal properties. Still another aspect of the invention relates to the preparation of said quaternized compounds and in still another aspect, the invention relates to the use of said compounds in several fields of application.

BACKGROUND OF THE INVENTION

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of creme rinses or conditioning treatments. Problems arise from the limited compatibility of anionic detergents with commercial cationic conditioning agents which precipitate out of solution in shampoo formulations.

Shampoo formulations have employed conventional anionic surfactants such as sodium lauryl sulfate, ammonium lauryl sulfate, ammonium lauryl ether sulfate and sodium lauryl ether sulfate which have been found to be incompatible with most cationic conditioning agents at effective concentration levels.

Additionaly, reproducible thickening for formulations containing anionic detergents such as sodium $\gamma$-olefin sulfonates is very difficult to achieve.

Still another problem encountered in hair conditioning shampoos is one of a preservative nature. It has been found that shampoos, containing inadequate preservative, on standing develop strands of pseudomonas aerouginosa which are clearly visible in the liquid and which may cause scalp infection. Consequently, separate biocidal agents are added to the formulation to prevent development of this bacteria and prevent skin infection. These and many other problems are encountered in the formulation of various shampoos, conditioners and cream rinses. Certain of these difficulties are also encountered in skin lotions, healing salves, mouthwashes, etc.

Accordingly it is an object of this invention to minimize or obviate the above problems while providing additional benefits in hair and skin treating formulations.

Another object of the invention is to provide novel quaternized nitrogen containing compounds having unique properties.

Another object is to provide novel quaternized nitrogen containing compounds having excellent hair conditioning and thickening properties when incorporated into a shampoo and having high compatibility with components of hair and skin treating formulations.

Another object is to provide an economical and commercially feasible methOd for the preparation of said novel quaternized nitrogen containing compounds.

Still another object is to provide processes for the use of said quaternized compounds.

These and other objects will become apparent from the following description and disclosure.

THE INVENTION

According to this invention there is provided quaternized compounds having unique properties and defined by the formula

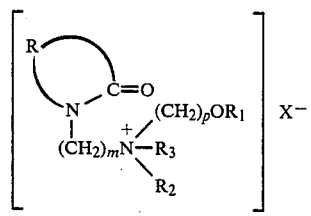

wherein m and p are each integers having a value of from 1 to 4; m is an integer having a value of from 1 to 4; R is alkylene having from 3 to 8 carbon atoms and is optionally substituted with $C_1$ to $C_4$ alkyl; $R_1$ is alkyl or alkenyl having from 1 to 30 carbon atoms; $R_2$ and $R_3$ are each independently selected from the group of —$(CH_2)_pOR_1$, alkyl, alkylhydroxy, aryl, aralkyl, aralkenyl, alkaryl and alkylene amidoalkyl radicals, said $R_2$ and $R_3$ groups having from 1 to 30 carbon atoms and at least one of $R_1$, $R_2$ and $R_3$ being a radical having from 8 to 30 carbon atoms; and $X_-$ is a chloride, bromide or iodide anion.

Preferred compounds within the above group are those wherein m is 1; R is —$CH_2$—$CH_2$—$CH_2$—; at least one of $R_2$ and $R_3$ is lower alkyl and $X_-$ is a chloride anion. The most preferred compounds of this group are those wherein at least one of $R_1$, $R_2$ and $R_3$ contains at least 8 carbon atoms in a linear chain. Examples of the compounds of this invention include:

N,N-dimethyl-N-[(2-pyrrolidonyl)methyl]-N-[3-(octyloxy) propyl]ammonium chloride N,N-dimethyl-N-[(2-pyrrolidonyl)methyl]-N-[2-(dodecyloxy) ethyl]ammonium chloride N,N-dibutyl-N-[(2-pyrrolidonyl)methyl]-N-[2-(tetradecyloxy) ethyl]ammonium chloride N-methyl-N-hydroxyethyl-N-[(2-pyrrolidonyl)methyl]-N-[3-(tetradecyloxy)propyl] ammonium chloride N-methyl-N-hydroxyethyl-N-[(2-pyrrolidonyl)methyl]-N-[3-(hexadecyloxy)propyl] ammonium chloride N,N-diphenyl-N-[(2-pyrrolidonyl)methyl]-N-[4-(octadecyloxy) butyl] ammonium chloride N,N-didodecyl-N-[(2-pyrrolidonyl)methyl]-N-[4-(ethoxy)butyl] ammonium chloride N-[(2-pyrrolidonyl)methyl]-N,N,N-tris[3-(dodecyloxy)propyl] ammonium chloride N-[(2-pyrrolidonyl)methyl]-N,N,N-tris[3-(decyloxy)propyl] ammonium chloride N-butyl-N-benzyl-N-[(2-pyrrolidonyl)methyl]-N-[2-(eicosyloxy)ethyl] ammonium chloride N-methyl-N-tolyl-N-[(2-pyrrolidonyl)methyl]-N-[2-(docosyloxy)ethyl] ammonium chloride N-phenyl-[(2-pyrrolidonyl)methyl]-N,N-bis[3-(decyloxy) propyl] ammonium chloride N-ethyl-[(2-pyrrolidonyl)methyl]-N,N-bis[3-(dodecyloxy) propyl] ammonium chloride
N-dodecyl-[(2-pyrrolidonyl)methyl]-N,N-bis[2-(ethyloxy) ethyl] ammonium chloride
N-propyl-[(2-pyrrolidonyl)methyl]-N,N-bis[2-(hexadecyloxy) ethyl] ammonium chloride
N-octadecyl-[(2-pyrrolidonyl)methyl]-N,N-bis[3-(octadecyloxy)propyl] ammonium chloride
N-propyl-N-styryl-[(2-pyrrolidonyl)methyl]-N-[4-(dodecyloxy) butyl] ammonium chloride
N-butyl-N-octadecyl-[(2-pyrrolidonyl)methyl]-N-[2-(allyloxy) ethyl] ammonium chloride.
N-propyl-N-ethylamidoethyl-[(2-pyrrolidonyl)methyl]-N-[4-(hexenyloxy)butyl] ammonium chloride
N,N-dimethyl-[(2-pyrrolidonyl)methyl]-N-[4-(dodecenyloxy) butyl] ammonium chloride
N,N-dimethyl-[(2-pyrrolidonyl)methyl]-N-[3-(tetradecenyloxy) propyl] ammonium chloride, etc.

However, it is to be understood that other halide salts of the following quaternary compounds represent examples also within the scope of this invention.

N-methyl-N-ethyl-[2-(2-pyrrolidonyl)ethyl]-N-[3-(dodecyloxy) propyl] ammonium salt
N-ethyl-N-hexadecyl-[4-(2-pyrrolidonyl)butyl]-N-[3-(octadecyloxy)propyl] ammonium salt
N,N-dimethyl-[2-(2-pyrrolidonyl)ethyl]-N-[3-(octyloxy) propyl] ammonium salt
N,N-dimethyl-[3-(2-pyrrolidonyl)propyl]-N-[4-(dodecenyloxy) butyl] ammonium salt
N-methyl-N-dodecyl-[4-(2-piperidonyl)butyl]-N-[3-(propyloxy) propyl] ammonium salt
N-hydroxyethyl-N-ethyl-[(2-piperidonyl)methyl]-N-[2-(decyloxy)ethyl] ammonium salt
N-benzyl-N-butyl-[4-(2-azacycloheptanonyl)butyl]-N-[3-(dodecyloxy)propyl] ammonium salt
N-benzyl-N-methyl-[(2-piperidinonyl)methyl]-N-[2-(octenyloxy)ethyl] ammonium salt
N-styryl-N-methyl-[(2-azacyclononanonyl)methyl]-N-[4-(hexadecyloxy)butyl] ammonium salt
N-phenyl-[(2-azacyclodecanonyl)methyl]-N,N-bis[3-(dodecyloxy)propyl] ammonium salt
N-hexylamidoethyl-N-methyl-[3-(2-piperidonyl)propyl](3-octadecyloxy)propyl] ammonium salt
N,N-dimethyl-N-[(2-azacyclononanoyl)methyl]-N-[3-(triacontyloxy)propyl] ammonium salt
N,N-didodecyl-N-[3-(2-azacycloheptanonyl)propyl]-N-[2-(ethyloxy)ethyl] ammonium salt
N,N-dibutyl-N-[4-(2-pyrrolidonyl)butyl]-N-[4-(tetradecenyloxy)butyl] ammonium salt
N-[2-(2-pyrrolidonyl)ethyl]-N,N,N-tris[2-(octadecyloxy) ethyl] ammonium salt
N-[4-(2-piperidonyl)butyl]-N,N,N-tris[2-(decenyloxy)ethyl] ammonium salt
N-[(2-azacycloheptanonyl)methyl]]-N,N,N-tris[4-(tetradecyloxy)butyl] ammonium salt
N,N-dibutylhydroxy-N-[(2-azacycloheptanonyl)methyl]-N-[3-(nonyloxy)propyl] ammonium salt
N,N-didecyl-N-[(2-azacyclononanoyl)methyl]-N-[3-(hexadecyloxy)propyl] ammonium salt
N-[(4-ethyl-2-azacyclononanoyl)methyl]-N,N,N-tris[4-(octadecyloxy)butyl] ammonium salt
N,N-dimethylamidoethyl-[(3,4-dimethyl-2-pyrrolidonyl)methyl]-N-[3-(octadecyloxy)propyl] ammonium salt
N-xylyl-N-[(3,4,5-tributyl-2-pyrrolidonyl)methyl]-N,N-bis[3-(hexadecyloxy)propyl] ammonium salt
N,N-dimethyl-N-[(4-methyl-2-piperidinonyl)ethyl]-N-[2-(hexadecyloxy)ethyl] ammonium salt
N-p-ethylphenyl-N-[(3,4,5-trimethyl-2-piperidonyl)methyl]-N,
N-bis-[3-(propyloxy)propyl] ammonium salt
N,N-tetradecyl-N-[(4-butyl-2-piperidonyl)methyl]-N-[3-(octyloxy)propyl] ammonium salt
N-(8-octamidooctyl)-N-[(4,5-diethyl-2-azacyclononanonyl) methyl]-N,N-bis[3-(dodecyloxy)propyl] ammonium salt and others.

The present quaternary compounds possess unique properties, among which is their ability to build viscosity, e.g. for liquids having a viscosity less than 50 centipoises, while simultaneously providing hair and skin conditioning capability in cosmetic formulations containing anionic surfactants. In the context of this application, "conditioning" includes the functions of moisturizing, softening, cleansing, penetrating, disinfecting, luster enhancing, hair combability, dye leveling, thickening, dye retention and others. These compounds are highly compatible with γ-olefin sulfonates and anionic surfactant salts conventionally employed in shampoos, skin lotions and textile treating products. Their compatibility is such that up to 5% by weight or more of the quaternized compounds can be incorporated in the formulation, a characteristic which permits the formation of effective formulations as liquids or gels. In contrast, most prior quaternary viscosity building conditioning compounds are incorporable only up to 0.5 or 1 wt. percent based on total anionic formulations. The pyrrolidonyl compounds which contain an octadecyl moiety on the quaternary nitrogen are particularly outstanding for their compatability, viscosity building and fiber and hair conditioning properties. The pyrrolidonyl products having a hexadecyl or dodecyl moiety on the quaternized nitrogen possess antibacterial properties and can be used in a mouthwash or as a highly compatible preservative in shampoo, hair conditioners and hand or body lotions. It is contemplated that mixtures of pyrrolidonyl compounds, such as those containing $C_{16}$ and $C_{18}$ alkyl terminally substituted compounds, can be employed in shampoos, hair conditioners, skin lotions and textile softeners as an agent which incorporates thickening, scroop, conditioning and preservative qualities in one additive; thus eliminating the need for separate chemical components to accomplish these individual needs. These mixtures may also be used to control dandruff or bacterial infections of the scalp and body skin Generally, the quaternary compounds of this invention are mixed with a standard formulation of shampoo, cream rinse, hand or body lotion or creams, mouthwash, etc., in an effective amount which ranges from between about 0.05 to about 8% by weight, preferably between about 0.5 and about 5% by weight, of the total formulation. The compatability of the present compounds with anionic γ-olefin sulfonates is surprising since most anionic compounds cause precipitation of cationic agents. However, the present compounds in concentrations up to 5% by weight show no tendency to precipitate after extended periods including periods up to 6 months or more.

The quaternary pyrrolidonyl compounds of this invention are prepared by an economically feasible process which involves the reaction between a tertiary ether amine and a N-haloalkyl lactam having a 5 to 10 membered ring. A general equation for the preparation is defined by the equation:

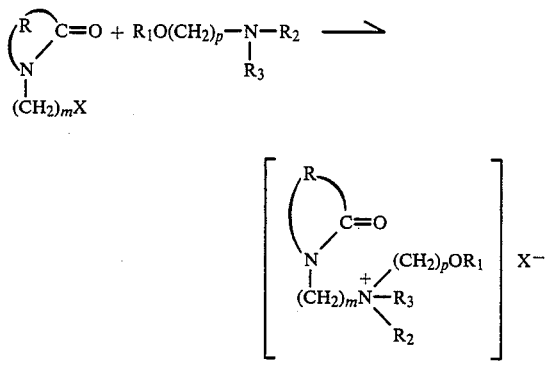

wherein m, p, R, $R_1$, $R_2$, $R_3$ and $X^-$ are as defined above and X is chloro, bromo or iodo.

Examples of suitable lactam reactants include the N-chloromethyl, N-bromomethyl and N-iodomethyl derivatives of 2-pyrrolidone, 4-methyl-2-pyrrolidone, 4-butyl-2-pyrrolidone, 2-piperidone, methyl-2-piperidone, 2-azacycloheptanone, 2-azacyclooctanone, 2-azacyclononanone, 2-azacyclodecanone and other $C_1$ to $C_4$ alkyl substituted derivatives bonded to an alkylene group in the heterocyclic ring of these lactams. Mixtures of these lactam reactants can also be employed to provide a correspondingly mixed quaternary product, if desired. Of these lactam reactants the N-halomethyl-2-pyrrolidones and N-halomethyl caprolactams are preferred and the N-chloromethyl lactams are most preferred.

The tertiary ether amines employed in the present process include reactive methyl and ethyl tertiary species containing at least one group having 8 to 22 carbon atoms, for example N-methyl-N,N-[3-di(decyloxy)propyl] amine, N,N-dimethyl-N-[3-(octadecyloxy)propyl] amine, N,N-dimethyl-N-[2-(dodecyloxy)ethyl] amine, N,N-dimethyl-N-[4-(hexadecyloxy)butyl] amine, N,N-dimethyl-N-[3-(eicosyloxy)propyl] amine, N-ethyl-N,N-[3-di(hexadecyloxy)propyl] amine and others including any of the ether amines corresponding to the forenamed quaternized products of this invention, e.g. N-phenyl-N,N-[3-di(decyloxy)propyl] amine, N-dodecyl-N,N-[2-di(ethoxy)ethyl] amine, N-(3-octadecanamidopropyl)-N,N-[2-di(methoxy)ethyl] amine, etc., ether amine based on mixtures of synthetic alcohols such as NEODOL 25 (a mixture of $C_{12}$ to $C_{15}$ primary alcohols, average molecular weight of 203), NEODOL 23 (a mixture of $C_{12}$ to $C_{15}$ primary alcohols, average molecular weight of 197) and cocoalcohol types such as ALFOL 810 (a mixture of $C_8$ and $C_{10}$ alcohols), ALFOL 1012 (a mixture of $C_{10}$, $C_{12}$ and $C_{14}$ alcohols), ALFOL 1216 (a mixture of $C_{12}$, $C_{14}$ and $C_{16}$ alcohols) and ALFOL 1218 (a mixture of $C_{12}$, $C_{14}$, $C_{16}$ and $C_{18}$ alcohols) etc. However, also included in the scope of this invention are reactive ether amines wherein a $C_8$ to $C_{30}$ group is itself substituted with alkoxy of 1 to 4 carbon atoms, phenyl, benzyl, amido, as well as tertiary ether amines having 1 to 2 aryl groups, e.g. phenyl, benzyl, tolyl, xylyl, etc., such as a bisphenyl ether amine, a ditolyl ether amine, a benzyl phenyl ether amine, and halo substituted phenyl ether amines. Tri-$C_8$ to $C_{22}$ alkoxyalkyl amines can also be employed in the reaction, examples of which include N,N,N-tris[3-(hexadecyloxy)propyl] amine, N,N,N-tris[4-(octadecyloxy)butyl] amine, N,N,N-tris[2-(dodecyloxy)ethyl] amine,
N,N,N-tris[3-(decyloxy)propyl] amine, etc.

The preferred ether amine reactants of this invention are those defined by the formula:

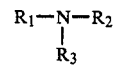

wherein $R_2$ is methyl, $R_3$ is methyl or $-(CH_2)_pOR_1$ and $R_1$ is $C_8$ to $C_{22}$ alkyl.

The process is effected by reacting the tertiary ether amine and the haloalkyl lactam at a temperature between about 25° and about 150° C., preferably between about 60° and about 100° C., under a pressure of from about 0 to about 50 psig, preferably atmospheric pressure, for a period up to about 10 hours, usually not more than 5 hours is required to complete the reaction From the above equation, it is seen that stoichiometric amounts of haloalkyl lactam and amino ether are used in the reaction. However, an excess of one or the other of the components is practicable in the process. Generally, for economic considerations, a mole ratio of between 1:1.5 and about 1.5:1 is employed; although, a slight excess of the tertiary ether amine to insure complete reaction of the lactam is recommended. Accordingly, the most preferred mole ratio of lactam to ether amine is about 1:1.01 and about 1:1.03.

It is also recommended that the haloalkyl lactam be added gradually or dropwise to the ether amine at the beginning of the ensuing exothermic reaction. At the completion of the reaction, the solid quaternized product is formed and recovered. Since the reaction is quantitative, the product can be used as is or, when a slight excess of the ether amine is employed, it can be neutralized with a weak acid such as acetic, lactic or citric acid.

For incorporating into a standard formulation of shampoo, cream rinse, hand or body lotion, dye bath or textile treating formulation, etc., the present product can be diluted with an inert diluent such as water, propylene glycol, ethanol, etc. The solution in the desired concentration can then be mixed into the formulation to provide a homogeneous liquid, gel, cream or lotion. However, since the present products in solvents are generally liquid at room temperature, they may be directly incorporated into a formulation. Incorporation of the present product is usually affected at room temperature under atmospheric pressure and requires no special formulating technique. However, for certain formulations incorporation of the present product can be effected at temperatures up to about 85° C. Amphoteric-containing shampoo formulations are best prepared by initially preparing an aqueous solution of the quaternized product and the amphoteric surfactant and then adding the solution to the shampoo formulation.

Having generally described the invention, reference is now had to the accompanying examples which set forth preferred embodiments, but which are not to be construed as limiting to the scope of the invention as more broadly set forth above and in the appended claims.

EXAMPLE I

To a 1 liter, 4-neck flask equipped with mechanical stirrer, reflux condenser, thermometer, and dropping funnel is added N,N-dimethyl-N-[3-(octadecyloxy) propyl] amine (0.505 mole) which is heated with stirring to 70° C. under $N_2$ blanket after which the heating source was removed and N-chloromethyl-2-pyrrolidone (0.5 mole) is added to the ether amine dropwise over a period of 25 minutes. An exothermic reaction ensues and is controlled at 100° C. by the rate of addition of N-chloromethyl-2-pyrrolidone. The yield of liquid N,N-dimethyl-N-[3-(octadecyloxy)propyl]-N-[(2-pyrrolidonyl)methyl] ammonium chloride is quantitative which is determined by titration. (Mercuric Acetate method as described by Sidney Siggia, "Quantitative Organic Analysis via Functional Group", 1963, 3d Ed., John Wiley & Sons, pages 552–554).

EXAMPLE II

The reaction of Example I is repeated except that the ether amine used is N,N-dimethyl-N-[2-(hexadecyloxy)ethyl] amine (2% molar excess with respect to N-chloromethyl-2- pyrrolidone). The product, N,N-dimethyl-N-[2-(hexadecyloxy)ethyl]-N-[(2-pyrrolidonyl)methyl] ammonium chloride is neutralized with acetic acid and recovered in quantitative yield.

EXAMPLE III

The reaction of Example II is repeated except that the ether amine used is N,N-dimethyl-N-[4-(tetradecyloxy)butyl] amine. The corresponding N,N-dimethyl-N-[4-(tetradecyloxy)butyl]-N-[(2-pyrrolidonyl) methyl]ammonium chloride is recovered in quantitative yield.

EXAMPLE IV

The reaction of Example II is repeated except that the ether amine used is N,N-dimethyl-N-[3-(dodecyloxy)propyl] amine. The corresponding N,N-dimethyl-N-[3-(dodecyloxy)propyl]-N-[(2-pyrrolidonyl) methyl]ammonium chloride is recovered in quantitative yield.

EXAMPLE V

The reaction of Example II is repeated except that the ether amine used is N,N-dimethyl-N-[3-(decyloxy)propyl] amine. The corresponding N,N-dimethyl-N-[3-(decyloxy)propyl]-N-[(2-pyrrolidonyl)methyl] ammonium chloride is recovered in quantitative yield.

EXAMPLE VI

The reaction of Example II is repeated except that the ether amine used is N-methyl-N-octadecyl-N-[3-(octyloxy)propyl] amine. The corresponding N-methyl-N-octadecyl-N-[3-(octyloxy)propyl]-N-[(2-pyrrolidonyl)methyl] ammonium chloride is recovered in quantitative yield.

EXAMPLE VII

The reaction of Example II is repeated except that the ether amine used is N,N-[3-di(octadecyloxy)propyl]-N-methyl amine. The corresponding N-methyl-N,N-[3-di(octadecyloxy)propyl]-N-[(2-pyrrolidonyl) methyl] ammonium chloride is recovered in quantitative yield.

EXAMPLE VIII

The reaction of Example II is repeated except that the ether amine used is N,N-didecyl-N-[2-(methyloxy)ethyl] amine. The product, N-[2-(methyloxy)ethyl]-N,N-didecyl-N-[(2-pyrrolidonyl)methyl] ammonium chloride is obtained in quantitative yield.

EXAMPLE IX

The reaction of Example II is repeated except that the ether amine used is N,N-dimethyl-N-[3-tridecyloxy)propyl] amine. The product, N,N-dimethyl-N-[(2-pyrrolidonyl)methyl]-N-[3-(tridecyloxy)propyl] ammonium chloride is obtained in quantitative yield.

EXAMPLE X

The reaction of Example II is repeated except that the lactam used is N-bromomethyl-2-caprolactam, the N,N-dimethyl-N-[2-(hexadecyloxy)ethyl]-N-[(2-azacycloheptanonyl)methyl] ammonium bromide is recovered as a solid product.

Other lactam containing products described herein are prepared by the general procedure outlined above with the substitution of the desired 2-pyrrolidonyl-, 2-piperidonyl-, 2-azacycloheptanonyl-, 2-azacyclocotanonyl-, 2-azacyclononanonyl-, or 2-azacyclodecanonyl- lactam reactant and/or the substitution of the desired tertiary ether amine.

Although all of the present quaternized compounds possess excellent surfactant properties, certain members are particularly recommended for incorporation into specific types of cosmetic formulations. Table I lists some of such uses for individual quaternized products within the scope of this invention, together with a brief description of the benefits derived from their incorporation.

Generally, the present products are added to the formulations in amounts between about 0.1 and about 5 wt. %, based on active ingredients. The quaternized compounds in Table I have the general formula:

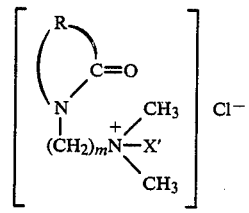

except No. 16 which has the formula:

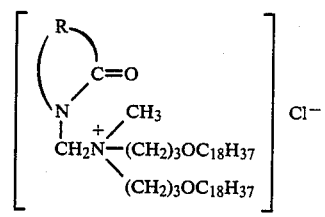

TABLE I

| No. | Compd where X' is | For Formulation In | Benefits Achieved |
|---|---|---|---|
| 1 | [3-(octadecyloxy)propyl] | cream rinse | improved wet/dry combing improved luster & shine |
| 2 | [4-(octadecyloxy)butyl] or [3-(15-octadecen-1-yloxy)propyl] | hair conditioner | improved wet/dry combing overall conditioning & improved luster & shine |
| 3 | [2-(hexadecyloxy)ethyl] | blow-dry styling lotion | protection from heat, improved luster, shine, body & overall conditioning, preservation and styling |
| 4 | [3-(alkyloxy)propyl]where | moisturizing lotion | facilitates rub-in, smoother feel & high |

TABLE I-continued

| No. | Compd where X' is | For Formulation In | Benefits Achieved |
|---|---|---|---|
| | alkyl is a mixture of $C_{12}$ to $C_{15}$ derived from NEODOL 25 | | compatability with other components |
| 5 | [3-(octadecyloxy)propyl] or [5,6-(diethyl)heptyl-1-yloxy)propyl] | bubble bath | high compatability, smooth after-feel & viscosity enhancement |
| 6 | [3-(dodecyloxy)propyl] | mouthwash | good germicidal properties clean, pleasant taste |
| 7 | [3-(octadecyloxy)propyl] | syndet bar | high compatability & improved feel |
| 8 | [4-(octadecyloxy)butyl] or [4-(11-dodecen-1-yloxy)butyl] | after-sun lotion | high compatability, smoother feel & facilitates rub-in |
| 9 | [2-(octadecyloxy)ethyl] | non-alcoholic mousse | conditioning, improved body, luster & shine, softer feel |
| 10 | [2-(octadecyloxy)methyl] | self-heating aerosol shave cream | high compatability, smoother skin feel, thermal stability & improved spreadability |
| 11 | [4-(octadecyloxy)butyl] | mousse hand & body lotion | improved rub-in and smoother after-feel |
| 12 | [3-(alkoxy)propyl] in which alkyl is a 50/50 mixture of $C_{12}$, $C_{14}$ and $C_{16}$ | mousse hand & body lotion | improved rub-in and smoother after-feel |
| 13 | compd. where X' is [3-(octadecyloxy)propyl] + compd where X' is [3-(hexadecyloxy)propyl] combined in n-dodecyl-2-pyrrolidone | conditioning shampoo | combined overall conditioning and cleaning, compatability with anionic components, improved wet/dry combing, luster & shine, viscosity enhancement & extra body |
| 14 | compd. where X' is [4-(octadecyloxy)butyl] in n-dodecyl-2-pyrrolidone | oily hair shampoo | "greaseless" conditioning, viscosity enhancement & improved wet/dry compatability, shine & luster |
| 15 | compd. where X' is [4-octadecyloxy)butyl] + compd where X' is [4-(hexadecyloxy)butyl] | hair mist conditioner | improved wet/dry combability, luster & shine, preservation and conditioning |
| | | hot oil treatment | improved conditioning, luster, shine, wet/dry combability, hair body & preservation |
| | | after shave balm | improved rub-in, skin conditioning & preservation and smoother skin feel |
| 16 | [3-di(octadecyloxy)propyl] | conditioning hair spray | dry compatability, improved luster, shine and manageability. |

Examples of specific formulations for the above uses achieving the benefits noted are presented as follows.

EXAMPLE XI

| Ingredients | Parts by Weight |
|---|---|
| CREAM RINSE | |
| Compound No. 1 in Table I | 2.0 |
| cetyl alcohol | 2.0 |
| emulsifying wax | 2.0 |
| citric acid | to pH 4 |
| deionized water | qs |
| fragrance | qs |
| preservative | qs |
| HAIR CONDITIONER | |
| Compounds No. 2 in Table I | 4.0 |
| PEG-8 Distearate | 2.5 |
| mineral oil | 1.5 |
| lanolin alcohol | 1.0 |
| stearic acid | 1.0 |
| PPG-20 methyl glucose ether | 1.0 |
| hydrolized animal protein | 0.25 |
| citric acid | to pH 4 |
| deionized water | qs |
| preservative | qs |
| fragrance | qs |
| BLOW DRY STYLING LOTION | |
| Compound No. 3 in Table I | 1.5 |
| ethanol | 3.0 |
| polyquaternium* 11 | 2.0 |
| PEG-10 Castor oil | 0.2 |
| fragrance | 0.2 |
| phosphoric acid | to pH 6 |
| deionized water | qs |
| CONDITIONING HAIR SPRAY | |
| Compound No. 16 in Table I | 0.6 |
| ethanol | 75.0 |
| ethyl ester of PVM/MA** copolymer | 4.1 |
| 2-amino-2-methyl-1-propanol 99% | 0.1 |
| fragrance | 0.2 |
| propellant | 20.0 |

*the quaternized ammonium polymer formed by reacting dimethyl sulfate and a copolymer of vinyl pyrrolidone and dimethylamino methylacrylate
**vinyl methyl ether/maleic anhydride

| Ingredients | Parts by Weight |
|---|---|
| CONDITIONING SHAMPOO | |
| Compounds of the type in Table I where X' is a mixture of | |
| [3-(dodecyloxy)propyl] and | 1.5 |
| [3-(tetradecyloxy)propyl] | 1.5 |
| N—dodecyl-2-pyrrolidone | 0.6 |
| polyquaternium 11 | 0.5 |
| sodium laureth-4-phosphate | 0.8 |
| ammonium lauryl sulfate | 40.0 |
| silk protein | 0.25 |
| tetrasodium ethylenediamine tetra-acetic acid | 0.2 |
| deionized water | qs |
| colorant | qs |
| fragrance | qs |
| MOISTURIZING LOTION | |
| Compound No. 4 in Table I | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |

| Ingredients | Parts by Weight |
| --- | --- |
| Oleth-20*** | 1.0 |
| triethanolamine 98% | 1.0 |
| deionized water | qs |
| preservative | qs |
| fragrance | qs |

*a mixture of methylated siloxane polymers end-blocked with trimethyl siloxy units (dimethylpolysiloxane)
**cross-linked polymer of acrylic acid
***PEG ether of oleyl alcohol

| Ingredients | Parts by Weight |
| --- | --- |
| BUBBLE BATH | |
| Compounds No. 5 in Table I | 3.0 |
| ammonium nonoynol-4-sulfate | 30.0 |
| sodium cocoyl isothionate | 10.0 |
| cocamidopropyl hydroxysultaine | 10.0 |
| cocamide diethanolamide | 6.0 |
| sodium methyl cocyl taurate | 20.0 |
| aloe vera gel | 1.0 |
| coconut oil | 1.0 |
| glycol stearate | 1.0 |
| deionized water | qs |
| preservative | qs |
| colorant | qs |
| SHAMPOO FOR OILY HAIR | |
| Compound No. 14 in Table I | 3.0 |
| n-dodecylpyrrolidone | 1.0 |
| tetrasodium ethylenediamine tetra-acetic acid | 0.2 |
| sodium lauryl sulfate | 20.0 |
| alpha-olefin sulfonate | 20.0 |
| polyquaternium 11 | 0.5 |
| deionized water | qs |
| preservative | qs |
| colorant | qs |
| fragrance | qs |
| added inorganic salts as desired for viscosity modification | |
| MOUTHWASH | |
| Compound No. 6 in Table I | 0.05 |
| alcohol, 190° | 20.00 |
| thymol | 0.03 |
| glycerine | 10.00 |
| flavor | 2.0 |
| distilled water | qs |
| polysorbate 80 | 2.00 |
| SYNDET BAR (Superfatted) | |
| Compound No. 7 in Table I | 0.5 |
| stearic acid, triple pressed | 32.00 |
| kettle soap | 9.80 |
| sodiumcocoyl isethionate | 49.00 |
| sodium methyl cocoyl taurate | 6.90 |
| citric acid, 50% aqueous | 0.60 |
| titanium dioxide | 0.20 |
| fragrance | 1.00 |
| WATER RESISTANT EMOLLIENT AFTER SUN LOTION | |
| Compounds No. 8 in Table I | 3.0 |
| mink Oil, Light Fraction | 11.00 |
| glyceryl stearate, self emulsifying | 1.00 |
| stearic acid | 2.50 |
| mineral oil and lanolin alcohol | 2.00 |
| myristyl myristate | 3.000 |
| mineral oil | 10.00 |
| PVP/Eicosene copolymer | 2.00 |
| triethanolamine | 0.70 |
| sorbitol | 3.00 |
| hydroxyethylcellulose | 0.30 |
| distilled water | qs |
| preservative | qs |
| fragrance | qs |
| NON-ALCOHOLIC CONDITIONING MOUSSE | |
| Compound No. 9 in Table I | 5.00 |
| PVP K-30 | 2.00 |
| Oleth-20 | 0.50 |
| fragrance | qs |
| deionized water | 77.50 |
| propellant A-46 | 15.00 |

Employed dual dispensing valve for metering oxidant from $H_2O_2$ container and reductant from aerosol can.

| Ingredients | Parts by Weight |
| --- | --- |
| SELF-HEATING AEROSOL SHAVING CREAM | |
| Compound No. 10 in Table I | 2.00 |
| stripped coconut fatty acid | 1.10 |
| sorbitol | 10.00 |
| stearic acid | 4.20 |
| PEG-40 soritan peroleate | 2.00 |
| triethanolamine | 3.00 |
| potassium hydroxide | 1.00 |
| potassium sulfite | 9.00 |
| fragrance | 0.80 |
| butyrated hydroxy toluene (BHT) | 0.01 |
| butyrated hydroxy anisole (BHA) | 0.01 |
| deionized water | qs |
| propellant | qs |
| HAIR MIST CONDITIONER (w/o added preservative) | |
| 50/50 Mixture No. 15 in Table I | 1.00 |
| propylene glycol dicaprylate/dicaprate copolymer | 0.30 |
| oleamidopropyl dimethylamine | 0.50 |
| deionized water | 98.2 |
| CATIONIC MOUSSE HAND/BODY LOTION (Used 85 Parts of the following formula to 15 parts propellant A-46) | |
| Compound No. 11 in Table I | 0.50 |
| acetylated polyoxyethylene lanolin | 2.00 |
| ethoxylated lanolin alcohols | 1.00 |
| glyceryl stearate, self-emulsifying | 5.50 |
| cetyl alcohol | 1.50 |
| mineral oil, 70 CTS | 1.50 |
| stearyl alcohol | 1.50 |
| glycerin | 3.00 |
| isopropyl myristate | 4.00 |
| dimethicone, 100 CTS | 2.00 |
| water | qs |
| preservative | qs |
| fragrance | qs |
| HOT OIL TREATMENT - (w/o added preservative) | |
| 50/50 mixture No. 15 in Table I | 1.50 |
| oleamidopropyl dimethyl amine | 1.00 |
| polyethylene glycol 6000 distearate | 2.00 |
| hexylene glycol | 4.00 |
| lactic acid, 88% | to pH 4.4 |
| color | qs |
| deionized water | qs |
| AFTER SHAVE BALM | |
| 50/50 mixture No. 15 in Table I | 1.00 |
| Carbomer 941 | 0.20 |
| tetrasodium ethylene diamine tetra-acetic acid | 0.10 |
| cetearyl alcohol* and polyethylene glycol ether of cetearyl alcohol | 2.50 |
| isopropyl myristate | 1.00 |
| Oleth-20 | 1 00 |
| methyl gluceth 20 | 2.00 |
| triethanolamine, 98% | 0.20 |
| propylene glycol | 3.00 |
| SDA denatured alcohol | 7.50 |
| PVP/dimethylaminoethyl methacrylate | 7.00 |
| fragrance | 1.00 |
| distilled water | qs |

*50/50 mixture of cetyl and stearyl alcohols

The above examples are representative or preferred embodiments of the present invention; however, it will be understood that other species of instant quaternized lactams can be substituted in the above formulations to provide the benefits indicated. Also, in the preparation of the quaternized lactams described in Examples I–IX, other lactam and/or tertiary amino ethers described herein can be substituted to provide the corresponding quaternized products which are also included within the scope of this invention. Particularly recommended among these substituted species are the halomethyl-2-caprolactam reactants and the alkyl amidoalkyl-substituted or hydroxyalkyl-substituted tertiary ether amine reactants which also provide useful bactericidal and viscosity enhancing properties.

What is claimed is:

1. The quaternized compound having the formula

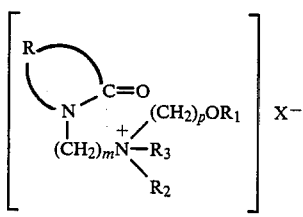

wherein $X^-$ is a chloride, bromide or iodide anion; m and p are each integers having a value of from 1 to 4; R is linear $C_3$ to $C_9$ alkylene in which alkylene may be substituted with lower alkyl; $R_1$ is alkyl or alkenyl having from 1 to 30 carbon atoms and $R_2$ and $R_3$ are each independently selected from the group consisting of $-(CH_2)_pOR_1$, alkyl, hydroxyalkyl, aryl, alkaryl, aralkyl, aralkenyl, and alkylene amidoalkyl radicals, said groups having up to 30 carbon atoms and at least one of $R_1$, $R_2$ and $R_3$ is a radical containing from 8 to 30 carbon atoms.

2. The quaternized compound of claim 1 wherein m has a value of 1; R taken together with —CO and —N— forms a pyrrolidonyl or a azacycloheptanonyl ring; $X^-$ is a chloride anion and $R_1$, $R_2$ and $R_3$ are alkyl.

3. The quaternized compound of claim 2 wherein at least one of $R_1$, $R_2$ and $R_3$ is alkyl having from 8 to 22 carbon atoms and another of $R_1$, $R_2$ and $R_3$ is methyl.

4. The quaternized compound of claim 3 which is the N,N-dimethyl-N-[(2-pyrrolidonyl)methyl]-N-[3-(octadecyloxy)propyl] ammonium salt.

5. The quaternized compound of claim 3 which is the N,N-dimethyl-N-[(2-pyrrolidonyl)methyl]-N-[3-(hexadecyloxy)propyl] ammonium salt.

6. The quaternized compound of claim 3 which is the N,N-dimethyl-N-[(2-azacycloheptanoyl)methyl]-N-[3-(octadecyloxy)propyl] ammonium salt.

7. The quaternized compound of claim 3 which is the N,N-dimethyl-N-[(2-piperidonyl)methyl]-N-[3-(dodecyloxy)propyl] ammonium salt.

8. The quaternized compound of claim 3 which is the N,N-diethyl-N-[(2-pyrrolidonyl)methyl]-N-[3-(octadecyloxy)propyl] ammonium salt.

9. The quaternized compound of claim 3 which is the N-methyl-N-[(2-pyrrolidonyl)methyl]-N,N-bis[3-(octadecyloxy)propyl] ammonium salt.

10. The process of adding an effective hair and skin conditioning amount of the compound of claim 1 to a hair and skin treating formulation.

11. The process of claim 10 which comprises additionally adding an effective preservative amount of N,N-dimethyl-N-[(2-pyrrolidonyl)methyl]-N-[3-(hexadecyloxy) propyl] ammonium salt to a shampoo formulation.

12. The process of adding between about 0.5 wt % and about 5 wt % of the compound of claim 1 to a shampoo formulation containing a surfactant selected from the group consisting of an alkali metal lauryl sulfate, an alkali metal lauryl ether sulfate, ammonium lauryl sulfate and an γ-olefin sulfonate.

13. The process of adding an effective antibacterial amount of the compound of claim 1 to a liquid subject to bacterial degradation.

14. The process of claim 10 wherein the hair and skin treating formulation is a hair or skin conditioning formulation.

15. The process of adding an effective skin softening amount of the compound of claim 1 to a skin treating composition.

16. The process of adding an effective skin moisturizing amount of the compound of claim 1 to a skin treating composition.

17. The process of adding an effective conditioning amount of the compound of claim 1 to a shampoo formulation.

18. The process of adding an effective fiber softening amount of the compound of claim 1 to a textile.

19. The process of claim 10 wherein the amount of said compound is effective to provide hair conditioning and preservative properties to said formulation.

* * * * *